United States Patent
Reddy et al.

(10) Patent No.: US 10,392,370 B2
(45) Date of Patent: Aug. 27, 2019

(54) PROCESS FOR THE PREPARATION OF DACLATASVIR DIHYDROCHLORIDE AND ITS INTERMEDIATES

(71) Applicant: Optimus Drugs Pvt Ltd, Hyderabad (IN)

(72) Inventors: Desi Reddy Srinivas Reddy, Hyderabad (IN); Peketi Subba Reddy, Hyderabad (IN)

(73) Assignee: OPTIMUS DRUGS PVT LTD, Hyderabad (IN)

( * ) Notice: Subject to any disclaimer, the term of this patent is extended or adjusted under 35 U.S.C. 154(b) by 0 days.

(21) Appl. No.: 15/599,526

(22) Filed: May 19, 2017

(65) Prior Publication Data

US 2018/0258078 A1    Sep. 13, 2018

(30) Foreign Application Priority Data

Mar. 13, 2017   (IN) .............................. 201741008659

(51) Int. Cl.
   *C07D 403/14*   (2006.01)
   *C07D 207/16*   (2006.01)

(52) U.S. Cl.
   CPC .......... *C07D 403/14* (2013.01); *C07D 207/16* (2013.01); *C07B 2200/13* (2013.01)

(58) Field of Classification Search
   CPC ........................... C07D 403/14; C07D 207/16
   See application file for complete search history.

(56) References Cited

U.S. PATENT DOCUMENTS

| 8,088,368 | B2 | 1/2012 | Guo et al. |
| 9,056,860 | B2 | 6/2015 | Scott et al. |
| 2013/0324496 | A1 | 12/2013 | Scott et al. |
| 2013/0324740 | A1 | 12/2013 | Scott et al. |

FOREIGN PATENT DOCUMENTS

| CN | 104530016 | | 4/2015 |
| CN | 105153128 | A * | 12/2015 |
| CN | 105461701 | | 4/2016 |
| WO | 20100132601 | | 11/2010 |
| WO | 2013184698 | | 12/2013 |
| WO | 2013184702 | | 12/2013 |
| WO | 2016178250 | | 11/2016 |

OTHER PUBLICATIONS

Machine translation of Chinese Patent Document CN 105153128, p. 1-16. (Year: 2015).*
Babu et al, MW-enhanced High-Speed Deprotection of Boc group using p-TsOH and Concommitant Formation of N-Me-Amino Acid Benzyl Ester p-TsOH salts, 2005, Synthetic Communications, vol. 35, p. 1795-1802. (Year: 2005).*

* cited by examiner

*Primary Examiner* — Karen Cheng
(74) *Attorney, Agent, or Firm* — Winthrop & Weinstine, P.A.

(57) ABSTRACT

The present invention relates to an improved process for the preparation of Daclatasvir dihydrochloride by using compound salt of formula (VIIc).

(VIIc)

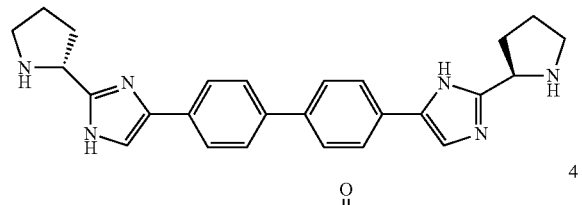
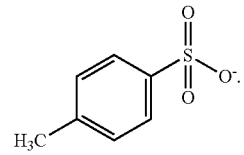

5 Claims, 1 Drawing Sheet

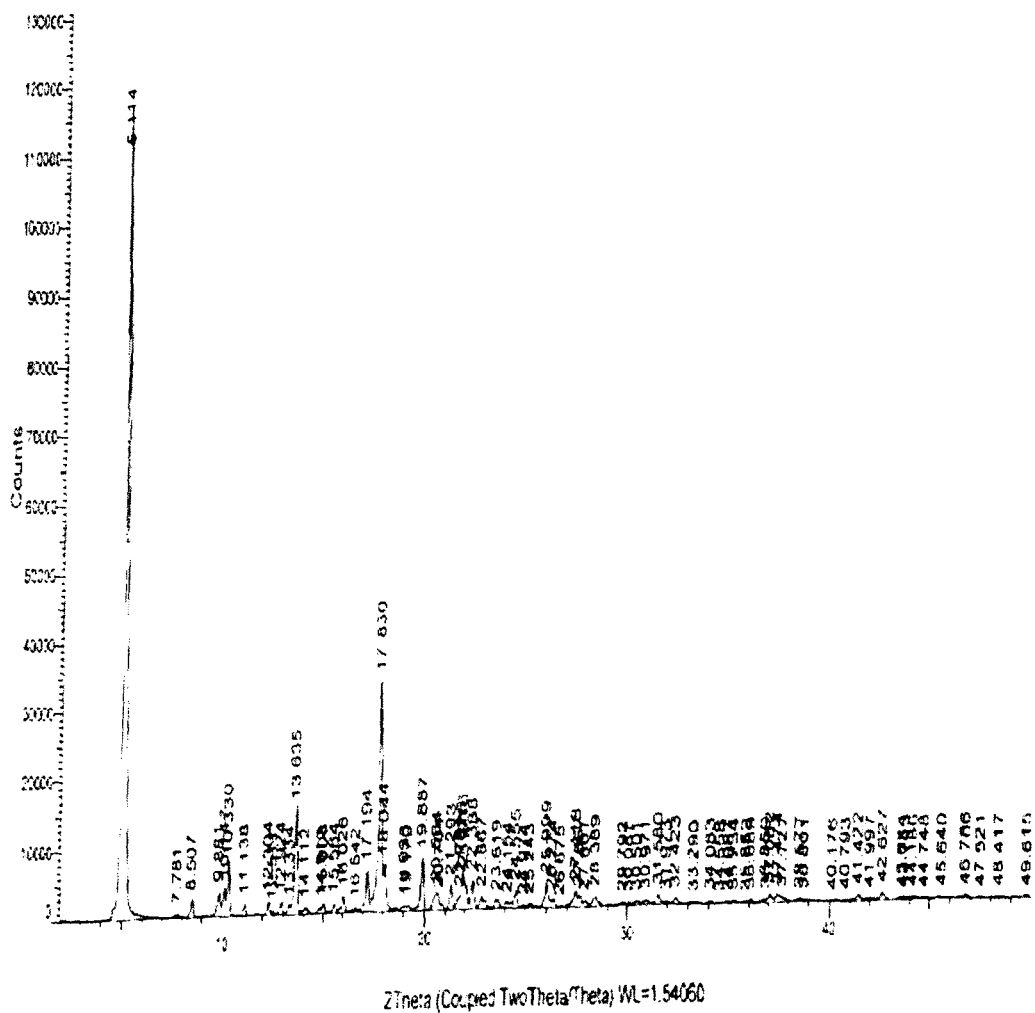

PROCESS FOR THE PREPARATION OF DACLATASVIR DIHYDROCHLORIDE AND ITS INTERMEDIATES

FIELD OF THE INVENTION

The present invention relates to an improved process for the preparation of Daclatasvir dihydrochloride by using compound salt of formula (VIIc).

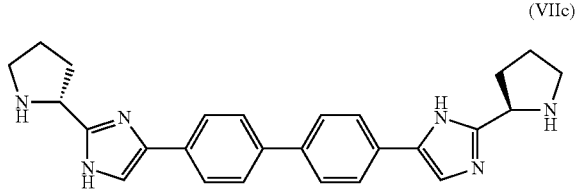

(VIIc)

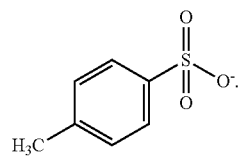

BACKGROUND OF THE INVENTION

Daklinza (trade name of Daclatasvir dihydrochloride) Daclatasvir is a drug for the treatment of hepatitis C (HCV), genotype 3 infections. Daclatasvir inhibits the HCV non-structural protein NS5A. Recent research suggests that it targets two steps of the viral replication process, enabling rapid decline of HCV RNA. Daclatasvir dihydrochloride is chemically known as methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl) carbamate dihydrochloride has the following structure.

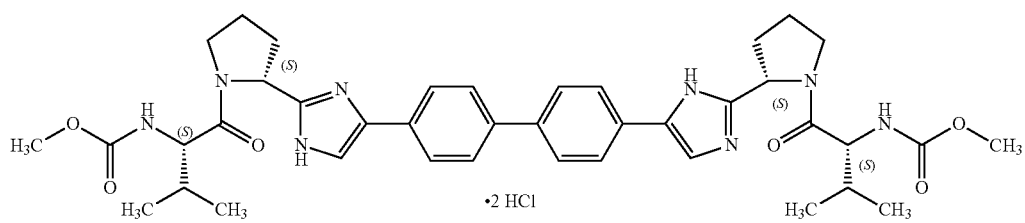

(I)

Daclatasvir dihydrochloride was first described in Example 24-23 of U.S. Pat. No. 8,329,159 B2, wherein the process is disclosed by reacting 1,1'-biphenyl-4,4'-diylbis(2-bromoethanone) with compound of formula (IV) in presence of base to produce compound of formula (V), further it was cyclized in presence of NH$_4$OAc and followed by deprotection in presence of acidic conditions to obtained compound of formula (VII). This on reacted with compound of formula (VIII) in presence of HOBt hydrate, DIPEA, EDC1.HCl and hydrochloric acid to get Daclatasvir dihydrochloride (I).

The above said process is schematically shown as below:

Scheme-I

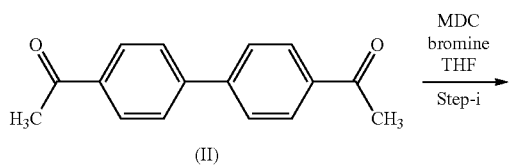

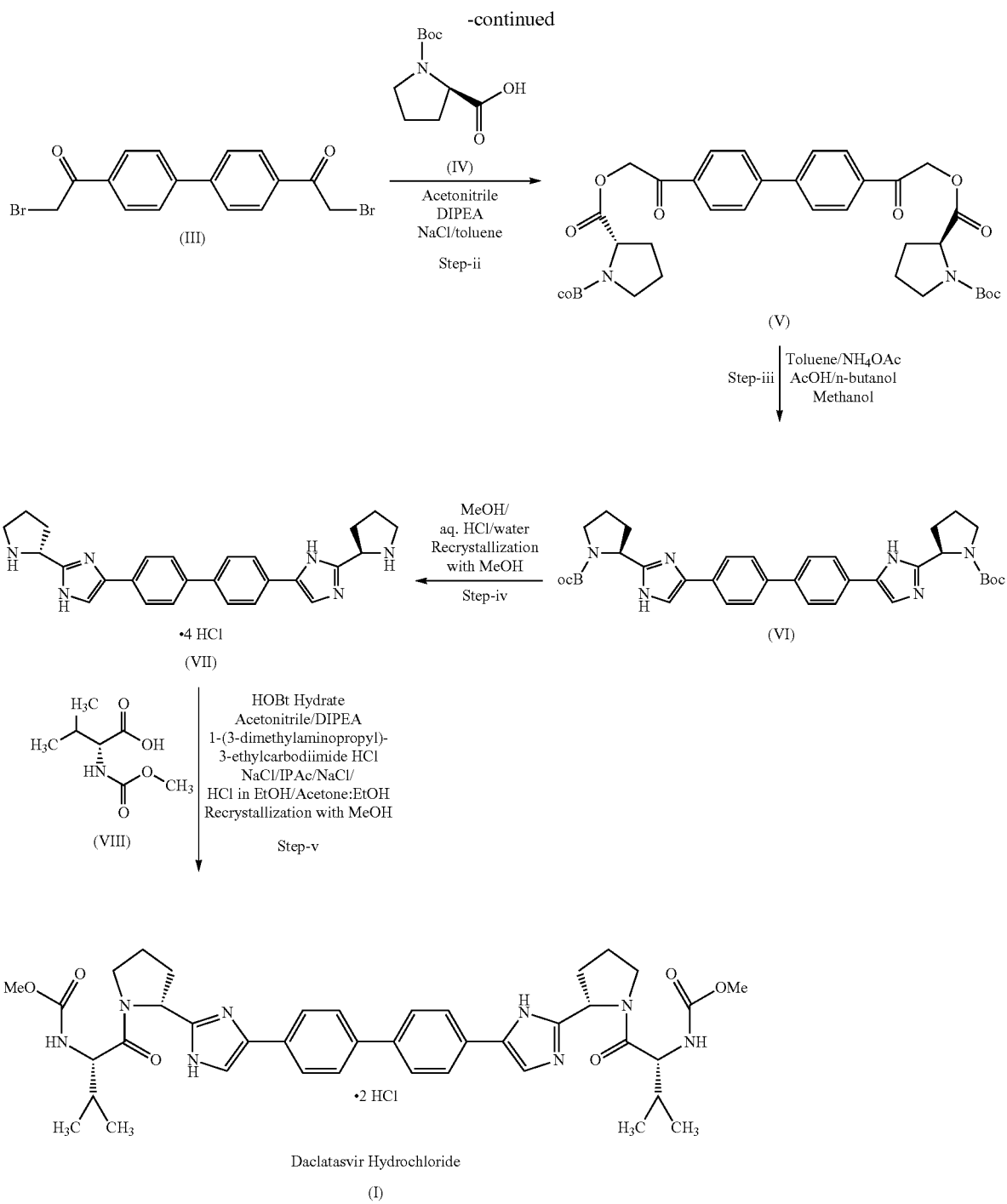

According to the above prior art processes which involves the condensation reaction of compound of formula (III) with 1-(tert-butoxycarbonyl)-L-proline in presence of base causes low yield and high impurity profile.

Hence, the use of base may not feasible and it is not economical for industrial scale for the preparation of Daclatasvir dihydrochloride (I).

WO 2016178250 discloses a process for the preparation of Daclatasvir dihydrochloride which is comprises compound of formula (IX) undergoes acetylation to get a compound of formula (X), this on followed by reacted with compound of formula (XI) to obtain a compound of formula (XII). The product of step ii is reacted with compound of formula (IVa) and followed by reacted with compound of formula (XI) to give a compound of formula (XIV), later reacted with compound of formula (IVa) to get a compound of formula (Va) further it converts into compound of formula (VIa), followed by deprotection and reacted with compound of formula (VIII) to obtain Daclatasvir dihydrochloride, which is depicted in the scheme-II given below:

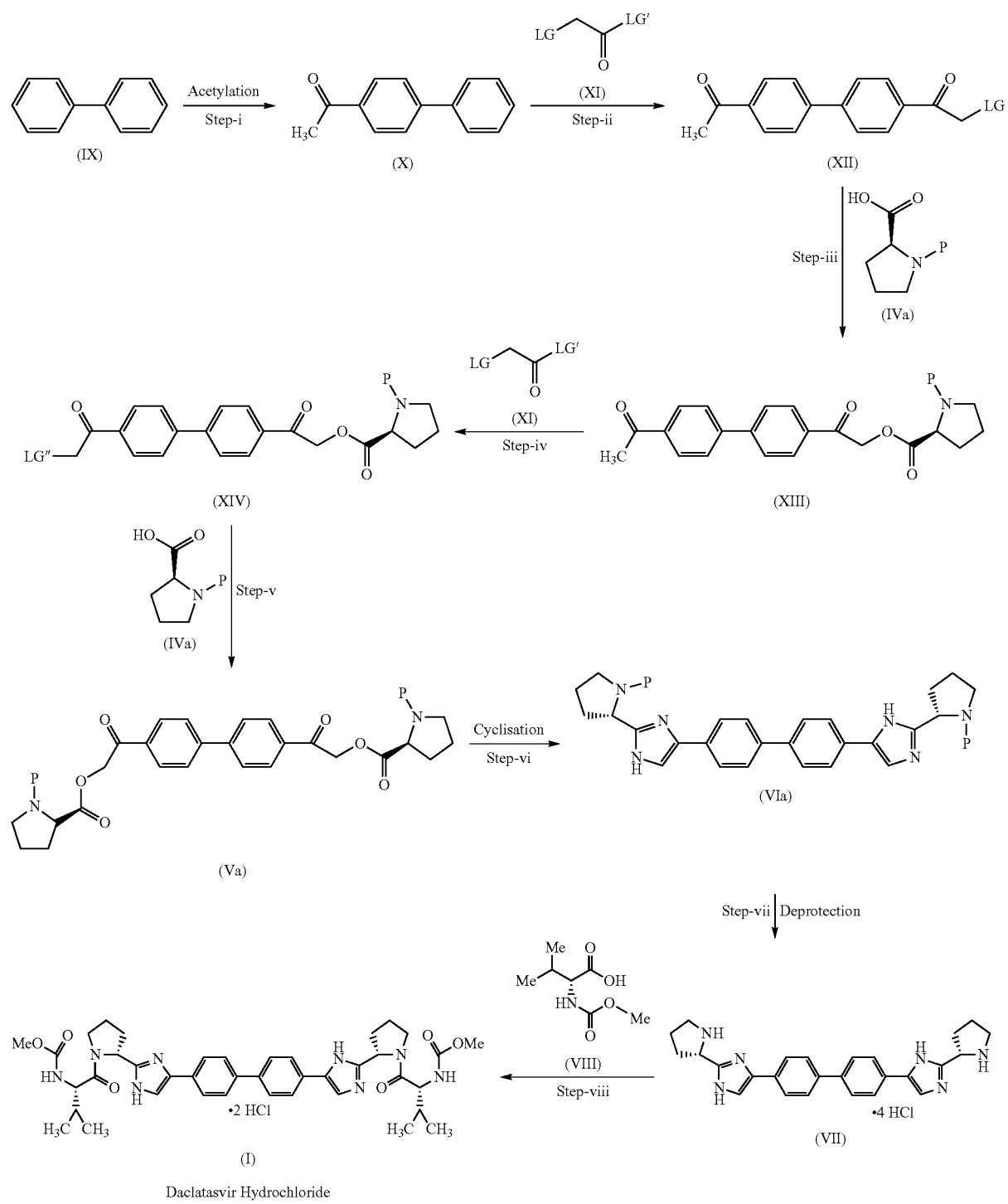

Scheme-II

The process of WO '250 discloses various disadvantages in the reaction management which has particularly more reactive steps for preparation of the Daclatasvir dihydrochloride on the industrial scale.

CN 105461701 A discloses process for the preparation of Daclatasvir dihydrochloride, which comprises the compound of formula (III) is reacted with compound of formula (XV) and followed by cyclisation in presence of ammonium acetate to get Daclatasvir dihydrochloride (I).

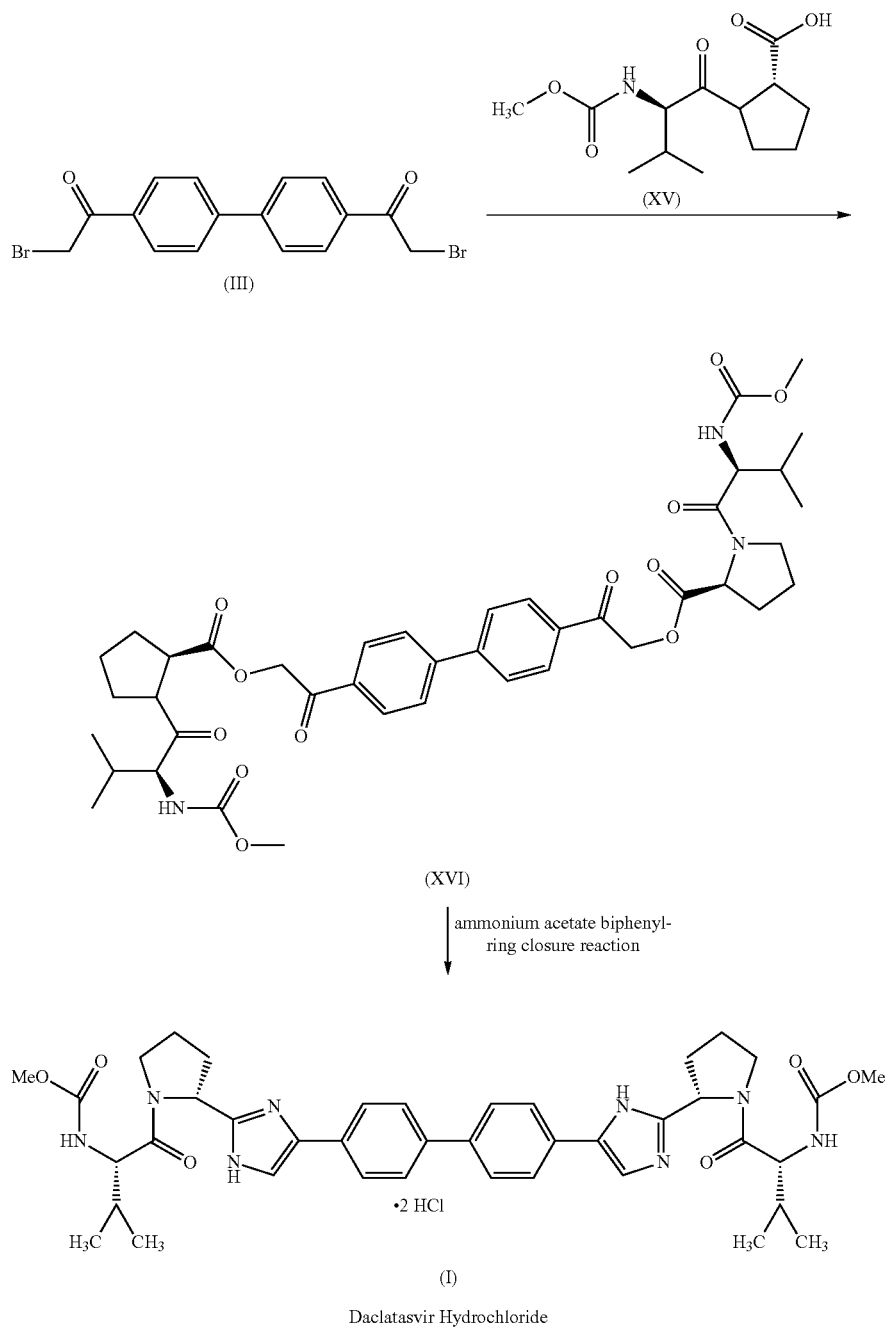

(I)

Daclatasvir Hydrochloride

In view of the foregoing, the present inventors have result of extensive studies, the efficiency is extremely only the condensation reaction of compound of formula (III) with potassium 1-(tert-butoxycarbonyl)-L-proline is carried out in absence of base, it was found that the corresponding (2R,2'R)—O'2,O2-([1,1'-biphenyl]-4,4'-diylbis(2-oxoethane-2,1-diyl))1-di-tert-butyl bis(pyrrolidine-1,2-dicarboxylate) can be produced in high yield and purity with advantages of low consumption of solvents.

The present inventors are also concluded that coupling reaction of PTSA salt of compound of formula (VIIc) with methoxy carbonyl L-valine of formula (VIII) is carried out in presence of coupling agent to affords Daclatasvir dihydrochloride with high purity, less impurity and good yield.

SUMMARY OF THE INVENTION

The present invention relates to an improved, commercially viable and industrially advantageous process for the preparation of Daclatasvir dihydrochloride.

In one aspect of the present invention provides an improved process for the preparation of Daclatasvir dihydrochloride (I), comprising the steps of:

a) 1,1'-biphenyl-4,4'-diylbis (2-chloroethanone) of formula (IIIa) is reacted with compound of formula (IVa) in absence of base to obtain compound of formula (V).

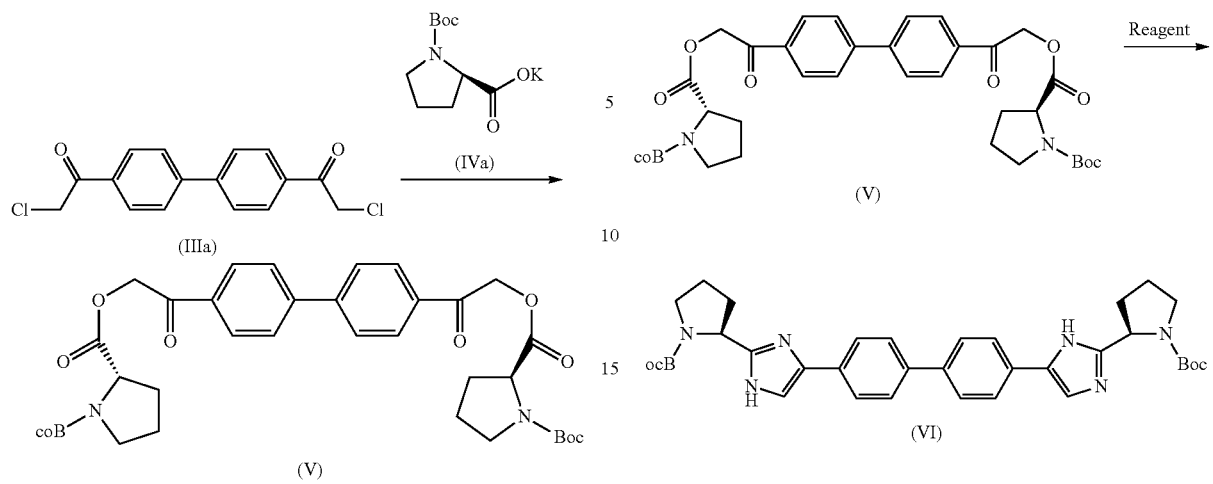

b) The product of step a) is cyclized in presence of reagent and solvent to obtain compound of formula (VI).

c) The product of step b) is deprotected in presence of acidic conditions to obtain compound of formula (VIIb).

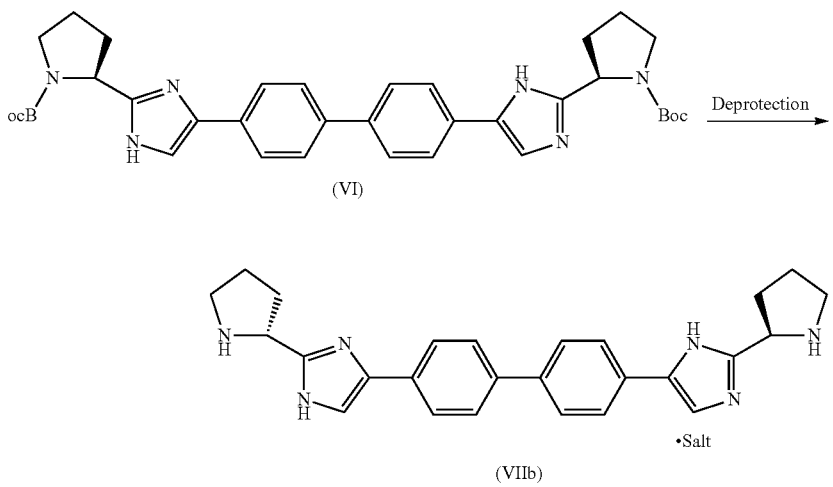

Salts are p-toluene sulphonic acid or oxalic acid or sulfamic acid d) The product of step c) is reacted with compound of formula (VIIb) in presence of coupling agent/base to get Daclatasvir and it reacts with hydrochloric acid to obtain Daclatasvir dihydrochloride of formula (I).

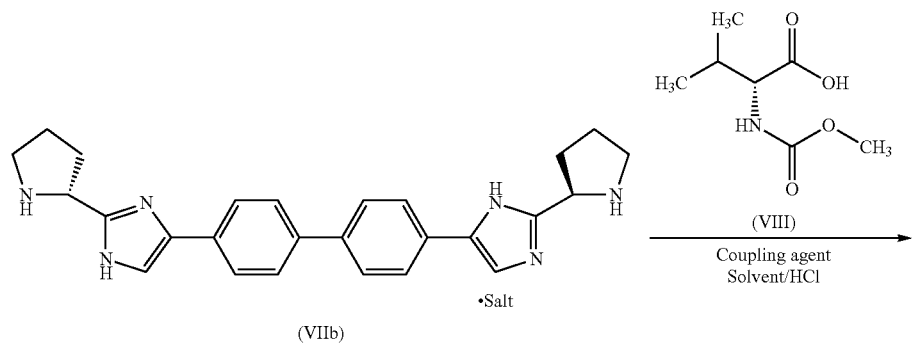

-continued

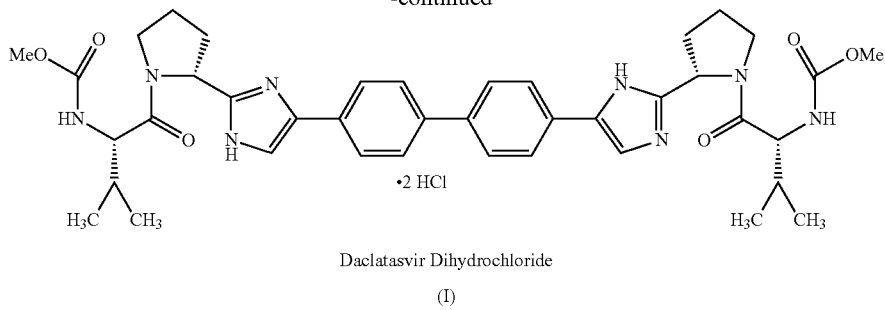

Daclatasvir Dihydrochloride
(I)

In another aspect of the present invention, a crystalline form of 4-(2-((R)-pyrrolidin-2-yl)-1H-imidazol-5-yl)-4'-(2-((S)-pyrrolidin-2-yl)-1H-imidazol-5-yl)-1,1'-biphenyl para toluene sulphonate of formula (VIIc), characterized by a PXRD pattern with peaks at about, 5.11, 10.33, 13.63, 17.83, 19.88, 21.91 and 25.99°+0.2° (2θ).

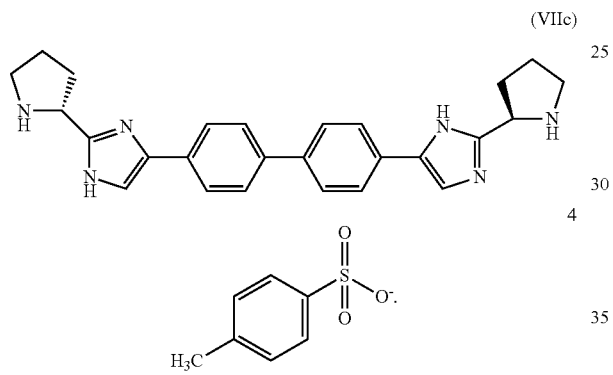

(VIIc)

BRIEF DESCRIPTION OF DRAWINGS

FIG. 1: depicts a powder X-ray diffractogram (PXRD) of crystalline form of compound of formula (VIIc)

DETAILED DESCRIPTION OF THE INVENTION

The present invention relates to an improved, commercially viable and industrially advantageous process for the preparation of Daclatasvir dihydrochloride In one embodiment of the present invention is relates to an improved process for the preparation of Daclatasvir dihydrochloride comprising the steps of:
a) 1,1'-biphenyl-4,4'-diylbis (2-chloro ethanone) of formula (IIIa) is reacted with compound of formula (IVa) in absence of base to obtain compound of formula (V).
b) The product of step a) is cyclized in presence of reagent and solvent to obtain compound of formula (VI).
c) The product of step b) is deprotected in presence of acidic conditions to obtain compound of formula (VIIb).
d) The product of step c) is reacted with compound of formula (VIIb) in presence of coupling agent/base to get Daclatasvir and it reacts with hydrochloric acid to obtain Daclatasvir dihydrochloride of formula (I).

According to an embodiment of the present invention, wherein 1,1'-biphenyl-4,4'-diylbis(2-chloroethanone) of formula (IIIa) is reacted with compound of formula (IVa) in absence of base and presence of solvent at room temperature, allow to stir and then raise the temperature at 40-60° C. for 3-6 hours, preferably 45 to 50° C. for 4-5 hours to obtain compound of formula (V) and its forward to cyclisation in presence of reagent and solvent at reflux condition for 5-9 hours to get a formula (VI); The compound of formula (VI) is deprotected in presence of acidic conditions at 20-40° C. under pH 7-10 (preferably 25-30° C. under pH 8-9) and stir for 30 minutes to get a precipitate solid. The obtain solid was filtered to get compound of formula (VIIb) and further it reacts with methoxy carbonyl L-valine of formula (VIII) at 0-20° C. (preferably 0-5° C.) in presence of coupling agent/base to get Daclatasvir and it reacts with hydrochloric acid in presence of isopropyl alcohol (IPA) at 20-40° C. for 30 minutes, to afford a Daclatasvir dihydrochloride of formula(I).

According to an embodiment of the present invention, solvents are selected from group comprising of dimethyl sulfoxide (DMSO), acetone, tetrahydrofuran (THF), dimethylformamide (DMF), acetonitrile, ethyl acetate, dichloromethane, toluene, xylene, mesitylene, acetic acid, methanol, ethanol, isopropanol and water.

According to an embodiment of the present invention, the cyclization has been taken place in presence of reagents are selected from ammonium acetate, ammonium formate, ammonium sulfamate, ammonium phosphate, ammonium citrate, ammonium carbamate and ammonia; preferably ammonium acetate; the bases are selected from triethylamine, diisopropylethylamine, and diisopropylamine; preferably triethyl amine.

According to an embodiment of the present invention, the acids are used in deprotection step is selected from p-toluene sulphonic acid, oxalic acid and sulfamic acid; preferably p-toluene sulphonic acid; the coupling agents are selected from 1,1'-carbonyldiimidazole, bis(2-oxo-3-oxazolidinyl) phosphinic chloride, 1-hydroxy-7-azabenzotriazole, 1-hydroxybenzotriazole hydrate, 3-hydroxy-1,2,3-benzotriazin-4 (3H)-one, 1-(3-dimethylaminopropyl)-3-ethylcarbodiimide hydrochloride, 4-nitrophenol, pentafluorophenol, 2-hydroxypyridine, N-hydroxysuccinimide, N-hydroxyphthalamide, 2-mercaptobenzoxazole, trimethylacetyl chloride, isobutylchloroformate, chloro dimethoxy triazole, oxalyl chloride, 2-hydroxypyridine-N-oxide, 5-nitro-2-hydroxy pyridine, and mixtures thereof.

In another embodiment of the present invention, a crystalline form of 4-(2-((R)-pyrrolidin-2-yl)-1H-imidazol-5-yl)-4'-(2-((S)-pyrrolidin-2-yl)-1H-imidazol-5-yl)-1,1'-biphenyl para toluene sulphonate of formula (VIIc) is characterized by a PXRD pattern with peaks at about, 5.11, 10.33, 13.63, 17.83, 19.88, 21.91 and 25.99±0.2° (2θ).

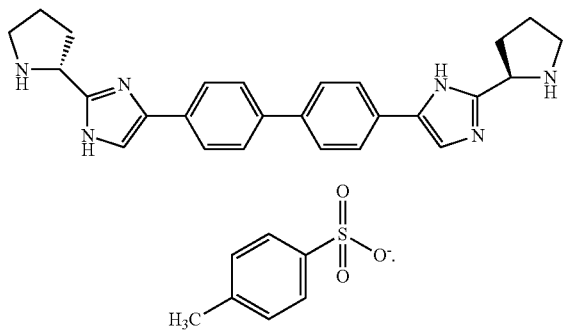

(VIIc)

The present inventors have result of extensive studies, the efficiency is extremely only the condensation reaction of compound of formula (III) with potassium 1-(tert-butoxycarbonyl)-L-proline is carried out in absence of base, it was found that the corresponding (2R,2'R)—O'2,O2-([1,1'-biphenyl]-4,4'-diylbis(2-oxoethane-2,1-diyl)) 1-di-tert-butyl-bis(pyrrolidine-1,2-dicarboxylate) can be produced in high yield and purity with advantages of low consumption of solvents.

The present inventors are also concluded that coupling reaction of PTSA salt of compound of formula (VIIc) with methoxy carbonyl L-valine of formula (VIII) is carried out in presence of coupling agent to afford Daclatasvir dihydrochloride with appreciable yield and high purity.

The following examples illustrate the present invention, but should not be construed as limiting the scope of the invention.

EXAMPLES

Preparation of Potassium (2S)-1-(tert-butoxycarbonyl)pyrrolidine-2-carboxylate

Example 1

Acetone (50 ml), (2S)-1-(tert-butoxycarbonyl)pyrrolidine-2-carboxylic acid (25 gm) and potassium t-butoxide (13 gm) were added into the flask at room temperature and the reaction mixture was stir and allow to cool at 20-25° C. Maintained reaction mixture under stir for 2-3 hours at 20-25° C. till it complies the reaction. The resultant white solid was filtered under nitrogen atmosphere, washed with acetone and dried under vacuum at 40-45° C. for 4-5 hours to obtain titled product.

Example 2

Tetrahydrofuran (150 ml), (2S)-1-(tert-butoxycarbonyl)pyrrolidine-2-carboxylic acid (25 gm) and potassium t-butoxide were added into the flask at room temperature. Raise the temperature of reaction mixture to 35-40° C. and maintained for 2-3 hours and the reaction mixture was stir and allow to cool at 20-25° C. Maintained reaction mixture under stir for 2-3 hours at 20-25° C. till it complies the reaction. The resultant white solid was filtered under nitrogen atmosphere, washed with tetrahydrofuran and dried under vacuum at 40-45° C. for 4-5 hours to obtain titled product.

Preparation of (2R,2'S)-di-tert-butyl 2,2'-(5,5'-([1,1'-biphenyl]-4,4'-diyl)bis(1H-imidazole-5,2-diyl))bis(pyrrolidine-1-carboxylate)

Example 3

In round bottomed flask, 1,1'-biphenyl-4,4'-diylbis(2-chloroethanone) (25 gm) and potassium (2S)-1-(tert-butoxycarbonyl)pyrrolidine-2-carboxylate (40 gm) were added into acetone (150 ml) at room temperature. The reaction mixture was allow to stir, followed by addition of (2.6 g) of sodium bromide and then raise reaction temperature at 45-55° C., maintained 4-5 hours at same temperature till it complies. If the reaction is completed, distilled out acetone under reduced pressure and cool the residual reaction mass to room temperature.

To the residual reaction mass, added toluene (300 ml) and purified water (150 ml) to separate layers. The resultant toluene layer was treated with ammonium acetate (98.5 gm) and allow to reflux at 110-120° C.; maintained for 6-8 hour under reflux condition till it complies. If the reaction is complies (checked by TLC), the reaction mass was cool to 50-60° C., followed by acetic acid and water (2:1) to separate layers. The separated aqueous layer was treated with sodium hydroxide solution (34 gm in 70 ml of water) in presence of methanol (13 ml) at 50-60° C. and stir the slurry for one hour at 50-60° C. The reaction mixture was cooled to 25-30° C. and stir for 1 hour at same temperature. The resultant solid was filtered, washed with methanol (10 ml)/N-methyl pyrolidine and methanol mixture (10 ml) and dried at 60-65° C. for 6-8 hours to obtain a title product.

Example 4

In round bottomed flask, 1,1'-biphenyl-4,4'-diylbis(2-chloroethanone) (25 gm) and potassium salt of BOC L-Proline (40 gm) were added into acetonitrile (150 ml) at room temperature. The reaction mixture was allow to stir, followed by addition of (2.6 g) of sodium bromide and then raise reaction temperature at 45-55° C. Maintained 4-5 hours at same temperature till it complies. If the reaction is completed, distilled out acetonitrile under reduced pressure and cool the residual reaction mass to 25-30° C.

To the residual reaction mass, added O-Xylene (300 ml) and purified water (150 ml), stir for 15 min and settle for 20 min to separate layers; the resultant xylene layer was treated with ammonium acetate (98.5 gm) and raise the reaction mass temperature and allow to reflux at 140-145° C., maintained for 6-8 hour under reflux condition till it complies. If the reaction is complies (checked by TLC), the reaction mass was cool to 50-60° C., followed by acetic acid and water (2:1) to separate layers. The separated aqueous layer was treated with sodium hydroxide solution (34 gm in 70 ml of water) in presence of methanol (13 ml) at 50-60° C. and stir the slurry for one hour at 50-60° C. The reaction mixture was cooled to 25-30° C. and stir for 1 hour at same temperature. The resultant solid was filtered, washed with methanol (10 ml)/N-methyl pyrolidine and methanol mixture (10 ml) and dried at 60-65° C. for 6-8 hours to obtain a title product.

Preparation of 4-(2-((R)-pyrrolidin-2-yl)-1H-imidazol-5-yl)-4'-(2-((S)-pyrrolidin-2-yl)-1H-imidazol-5-Yl)-1, 1'-biphenylpara toluene sulphonate Example 5

A mixture of methanol (250 ml), (2R,2'S)-di-tert-butyl 2,2'-(5,5'-([1,1'-biphenyl]-4,4'-diyl)bis (1H-imidazole-5,2- diyl))bis(pyrrolidine-1-carboxylate) (50 gm), para toluene sulphonic acid (75 gm) and purified water (100 ml) was stirred at 25-30° C. The reaction mass was raised to temperature at 60-70° C. for 8-10 hours and then allowed to cool at 10-15° C. to get a precipitate solid. The resultant solid was filtered, washed with methanol (50 ml) and taken the wet solid into purified water (500 ml) by adjusting pH to 8.0-9.0, followed by 5% sodium carbonate solution and allow to stir at 25-30° C. for 30 min to get a solid material. The resultant solid was filtered, washed with water and dried at 60-65° C. for 5-6 hours to afford a titled product of 4-(2-((R)-pyrrolidin-2-yl)-1H-imidazol-5-yl)-4'-(2-((S)-pyrrolidin-2-yl)-1H-imidazol-5-yl)-1,1'-biphenyl para toluene sulphonate.

Example 6

A mixture of 1,4-dioxane (500 ml), (2R,2'S)-di-tert-butyl 2,2'-(5,5'-([1,1'-biphenyl]-4,4'-diyl)bis (1H-imidazole-5,2-diyl))bis(pyrrolidine-1-carboxylate) (100 gm), para toluene sulphonic acid (150 gm) and purified water (200 ml) was stirred at 25-30° C. The reaction mass was raised to temperature at 60-70° C. for 8-10 hours and then allowed to cool at 10-15° C. to get a precipitate solid. The resultant solid was filtered and washed with methanol lot-2 (100 ml), dried at 60-70° C. for 5-6 hours to afford a titled product of 4-(2-((R)-pyrrolidin-2-yl)-1H-imidazol-5-yl)-4'-(2-((S)-pyrrolidin-2-yl)-1H-imidazol-5-yl)-1,1'-biphenyl para toluene sulphonate.

Example 7

A mixture of acetone (500 ml), (2R,2'S)-di-tert-butyl 2,2'-(5,5'-([1,1'-biphenyl]-4,4'-diyl)bis(1H-imidazole-5,2-diyl))bis(pyrrolidine-1-carboxylate) (100 gm), para toluene sulphonic acid (150 gm) and purified water (200 ml) was stirred at 25-30° C. The reaction mass was raised to temperature at 60-70° C. for 8-10 hours and then allowed to cool at 10-15° C. to get a precipitate solid. The resultant solid was filtered and washed with methanol lot-2 (100 ml), dried at 60-70° C. for 5-6 hours to afford a titled product of 4-(2-((R)-pyrrolidin-2-yl)-1H-imidazol-5-yl)-4'-(2-((S)-pyrrolidin-2-yl)-1H-imidazol-5-yl)-1,1'-biphenylpara para toluene sulphonate.

Example 8

A mixture of ethyl acetate (500 ml), (2R,2'S)-di-tert-butyl 2,2'-(5,5'-([1,1'-biphenyl]-4,4'-diyl)bis (1H-imidazole-5,2-diyl))bis(pyrrolidine-1-carboxylate) (100 gm), para toluene sulphonic acid (150 gm) and purified water (200 ml) was stirred at 25-30° C. The reaction mass was raised to temperature at 60-70° C. for 8-10 hours, and then allowed to cool at 10-15° C. to get a precipitate solid. The resultant solid was filtered and washed with methanol lot-2 (100 ml), dried at 60-70° C. for 5-6 hours to afford a titled product of 4-(2-((R)-pyrrolidin-2-yl)-1H-imidazol-5-yl)-4'-(2-((S)-pyrrolidin-2-yl)-1H-imidazol-5-yl)-1,1'-biphenyl para toluene sulphonate.

Preparation of Methyl((1S)-1-(((2S)-2-(5-(4'-(2-((2S)-1-((2S)-2-((methoxycarbonyl)amino)-3-methylbutanol)-2-pyrrolidinyl)-1H-imidazol-5-vl)-4-biphenylyl)-1H-imidazol-2-vl)-1-pyrrolidinyl) carbonyl)-2-methylpropyl)carbamate dihydrochloride (Daclatasvir Dihydrochloride)

Example 9

In round bottomed flask, 21.0 gm of methoxycarbonyl L-valine was dissolved into 300 ml dichloromethane and stirred at 0-5° C., followed by addition of 15.0 gm 1-hydroxybenzotriazole (HOBT), 21.0 gm 1-ethyl-3-(3-dimethylaminopropyl)carbodiimide (EDC.HCl) at same temperature and stir for 10 minutes. Added 50 gm of 4-(2-((R)-pyrrolidin-2-yl)-1H-imidazol-5-yl)-4'-(2-((S)-pyrrolidin-2-yl)-1H-imidazol-5-yl)-1,1'-biphenyl para toluene sulfonate to the clear solution and the mixture was allow to cool at 0-5° C. Then slowly added 22.0 gm of triethylamine and stir at same temperature condition till completion of the reaction. If the reaction is complies (checked by TLC), purified water added to the reaction mass to separate the layers.

The resultant dichloromethane layer was distilled under reduced pressure to get a residue, further it was treated with hydrochloric acid in presence of isopropyl alcohol (75 ml) at 45-50° C., stirred for 30 minutes and allow to cool at 25-30° C. under stir conditions to get a solid. The resultant solid was filtered and wash with isopropyl alcohol, later the wet solid was suspended in 200 ml methanol and allow refluxing at 50-60° C. to get a clear solution. Optionally added 2.5 gm charcoal to the clear solution stir and filter through hyflo bed. The obtain filtrate was added to 150 ml of methanol and stir for 30 minutes at 50 to 60° C., followed by slow addition 300 ml of isopropyl alcohol, allow to stir for one hour at 25 to 30° C. to get a solid. The resultant solid was filtered, washed with IPA and dried at 65-75° C. to obtain a titled product.

Example 10

In round bottom flask, 42.0 gm methoxycarbonyl L-valine was dissolved into of 300 ml of dimethyl formamide and stirred at 0-5° C., followed by addition of 30.0 gm 1-hydroxy benzotriazole (HOBT), 42.0 gm 1-ethyl-3-(3-dimethylaminopropyl) carbodiimide (EDC.HCl) at same temperature and stir for 10 minutes. Added 100 gm of 4-(2-((R)-pyrrolidin-2-yl)-1H-imidazol-5-yl)-4'-(2-((S)-pyrrolidin-2-yl)-1H-imidazol-5-yl)-1,1'-biphenyl para toluene sulphonate to the clear solution and the mixture was allow to cool at 0-5° C., then slowly added 50 gm of diisopropylethylamine and stir at same temperature conditions till completion of the reaction. If the reaction is complies (checked by TLC), purified water and dichloromethane added to the reaction mass to separate the layers.

The resultant dichloromethane layer distilled under reduced pressure to get a residue, further it was treated with hydrochloric acid in presence of isopropyl alcohol (150 ml) at 50-60° C., stirred for 30 minutes and allow to cool at 25-30° C. under stir conditions to get a solid. The resultant solid was filtered and wash with isopropyl alcohol, later the wet solid was suspended in 400 ml methanol and allow refluxing at 50-60° C. to get a clear solution. Optionally added 3 gm charcoal to the clear solution stir and filter through hyflo bed. The obtain filtrate was added to 50 ml of methanol and stir for 30 minutes at 50 to 60° C., followed by slow addition 600 ml of isopropyl alcohol, allow to stir for one hour at 25 to 30° C. to get a solid. The resultant solid was filtered, washed with IPA and dried at 65-75° C. to obtain a titled product.

We claim:
1. An improved process for the preparation of Daclatasvir dihydrochloride of formula (I) which comprises the steps of:
   a. 1,1'-biphenyl-4,4'-diylbis(2-chloroethanone) of formula (Ma) is reacted with compound of formula (IVa) in absence of base to obtain compound of formula (V);

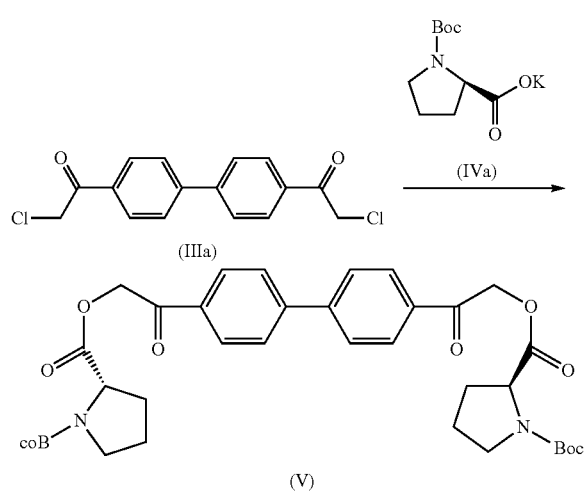

b. The product of step a) is cyclized in presence of a cyclisation agent to obtain compound of formula (VI);

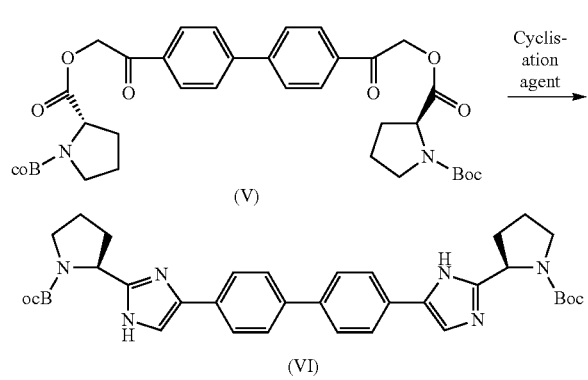

c. The product of step b) is deprotected in presence of p-toluene sulphonic acid at 20-40° C. to obtain compound of formula (VIIc);

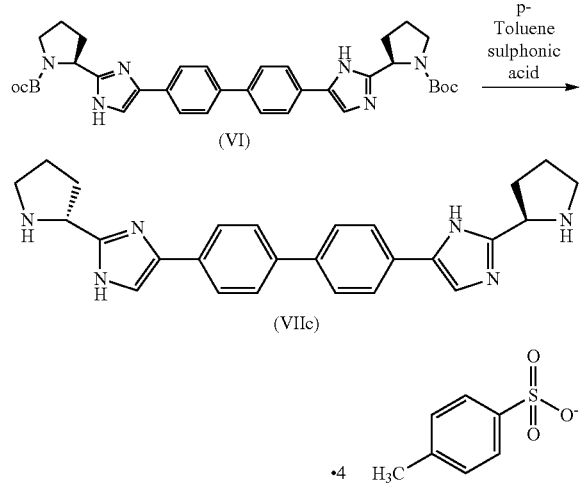

d. The product of step c) is reacted with compound of formula (VIII) in presence of coupling agent/base to get Daclatasvir and it reacts with hydrochloric acid to obtain Daclatasvir dihydrochloride of formula (I)

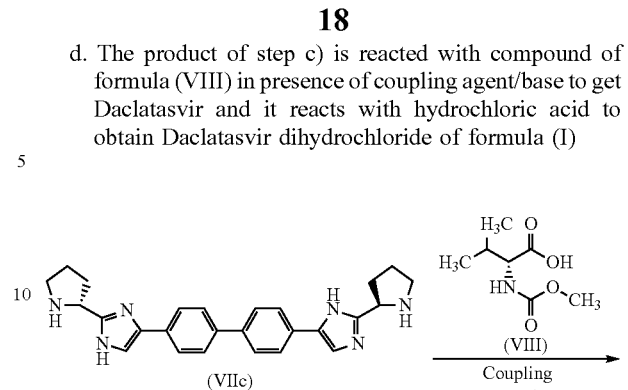

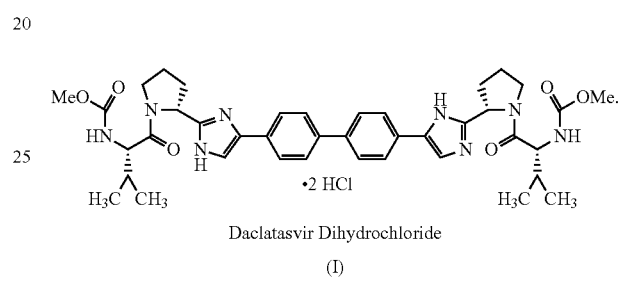

Daclatasvir Dihydrochloride
(I)

2. The process as claimed in claim 1, wherein the reaction steps a, b, c, and d are carried out in the presence of a solvent selected from dimethyl sulfoxide (DMSO), acetone, tetrahydrofuran (THF), dimethylformamide (DMF), acetonitrile and ethyl acetate, dichloromethane, toluene, xylene, mesitylene, acetic acid, methanol, ethanol, isopropanol and water.

3. The process as claimed in claim 1, wherein the cyclisation agent is selected from ammonium acetate, ammonium formate, ammonium sulfamate, ammonium phosphate, ammonium citrate, ammonium carbamate and ammonia, preferably ammonium acetate.

4. The process as claimed in claim 1, wherein the coupling agents are selected from 1,1'-carbonyldiimidazole, bis(2-oxo-3-oxazolidinyl)phosphinic chloride, 1-hydroxy-7-azabenzotriazole, 1-hydroxybenzotriazole hydrate (HOBt hydrate), 3-hydroxy-1,2,3-benzotriazin-4(3H)-one, 1-(3-dimethyaminopropyl)-3-ethylcarbodiimide hydrochloride (EDC HCl), 4-nitrophenol, pentafluorophenol, 2-hydroxypyridine, N-hydroxy succinimide, N-hydroxyphthalamide, 2-mercaptobenzoxazole, trimethylacetyl chloride, isobutylchloroformate, chlorodimethoxytriazole, oxalyl chloride, 2-hydroxypyridine-N-oxide, 5-nitro-2-hydroxypyridine, and mixtures thereof.

5. The process as claimed in claim 1, wherein the base is selected from triethylamine, diisopropylethylamine, and diisopropylamine.

* * * * *